United States Patent [19]

McRae

[11] Patent Number: Plant 5,964

[45] Date of Patent: Apr. 28, 1987

[54] ASIATIC LILY NAMED GOLD MEDAL

[75] Inventor: Edward A. McRae, Boring, Oreg.

[73] Assignee: Melridge, Inc., Gresham, Oreg.

[21] Appl. No.: 710,592

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of Asiatic hybrid lily bearing compact racemes of flowers of excellent form and large size, and having an intense and unusual color pattern, particularly characterized by the unusual combination of yellow and gold color tones and the very light maculation on each side of the nectaries at the base of the outer tepals, the color pattern being unique in the upright Asiatic division of lilies. The plant is an excellent garden plant, highly resistant to disease and showing high tolerance to virus, and its bulbs may be precooled and forced for cut-flower production, producing flowers early in the Asiatic lily season, thereby extending the cut-flower production season.

1 Drawing Figure

BACKGROUND OF THE NEW PLANT

This new variety of lily plant originated as a seedling selected from a group of seedlings produced as a result of breeding efforts carried on by me at Sandy, Oreg., since the year 1965 when the cross was made which produced the maternal parent of this new variety. In this case, the breeding efforts were carried on with the objective of producing superior upright-flowering Asiatic lilies in the shades of yellow and gold particularly suited to cut-flower production, thereby representing a range of flowering times to extend the season of cut-flower production.

The seed parent for this new Asiatic lily variety is a complex hybrid with the parentage "Uncle Sam"×[("Mega"×"Lemon Queen")×"Edith Cecilia"]. I achieved the desired objective by crossing this complex hybrid with the cultivar "Connecticut King" as the pollen parent.

In addition to their large size, the flowers of my new lily plant are characterized by having very broad and thick textured tepals, and an unusual color pattern in which each yellow tepal is lightly flushed with gold in its base portion adjacent the nectary and the rather small spotting maculae occur on each side of the nectary channel.

This new variety of lily plant has been asexually reproduced by me and under my direction at Sandy, Oreg., and the clones of this new plant, as observed at Sandy, Oreg., show that the new plant is vigorous and is a good grower and propagator having the desirable characteristics of hybrid vigor, great hardiness, and a high degree of disease resistance possessing all of the desired characteristics of form, color, and habit. Propagation of this new plant through successive generations by bulb scale propagation and natural propagation from bulblets has demonstrated that the novel and distinctive characteristics of the new plant hold true under asexual propagation from generation to generation and appear to be firmly fixed.

DESCRIPTION OF THE DRAWING

My new variety of Asiatic lily plant is illustrated by the accompanying photographic drawing which shows a fully opened bloom and illustrates the flower form, the unusually broad base portion of the lower tepals, and the tepal arrangement; the open bloom having been hand-painted to show, in particular, the novel and distinctive yellow and gold pattern and the very light comparatively inconspicuous maculation of the flower.

DESCRIPTION OF THE NEW VARIETY

The following is a detailed description of my new variety of Asiatic hybrid lily, with color designations according to The R.H.S. Colour Chart published by The Royal Horticultural Society of London, England, in 1966, the nomenclature being according to The Second Edition of The International Lily Register of The Royal Horticultural Society.

THE PLANT

Origin: Seedling.

Parentage:

*Seed parent.*—A complex unnamed hybrid having the parentage "Uncle Sam"×[("Mega"×"Lemon Queen")×"Edith Cecilia"] (unpatented).

*Pollen parent.*—"Connecticut King" (unpatented).

Horticultural classification: Hybrid lily cultivar, Division I-A of the Horticultural Classification of Lilies, by The Royal Horticultural Society.

Commercial classification: Upright Asiatic hybrid lily.

Form: Single stem, erect and stately.

Height: About 80 to 100 cm. from bulbs about 12 to 15 cm. in circumference.

Growth: Vigorous, sturdy, and upright.

Foliage:

*Quantity.*—Abundant.

*Leaf size.*—About 6 to 10 cm. long and about 1.5 to 2 cm. wide in the base portion.

*Leaf shape.*—Lanceolate with acute tip and entire margins.

*Texture.*—Leathery.

*Aspect.*—Glossy.

*Color.*—Light to medium green.

Bulbs:

*Size.*—Ranging up to 25 cm. in circumference in commercial use.

*Color.*—White.

THE BUD

Form: Long ovoid to oblong with obtuse base and tip.
Size: About 7 to 9 cm. long just prior to opening.
Opening rate: The bud opens slowly at maturity (about one hour) in response to light.
Color: Medium to deep yellow when outer tepals first divide and when tepals begin to unfurl.
Peduncle:
*Length.*—About 7 to 10 cm. depending upon light levels.
*Color.*—Medium green.

THE FLOWER

Blooming habit: Annually, once in early mid-season for Asiatic lilies. October-dug bulbs, properly precooled, planted in February in western Oregon under glass and with no supplementary lighting, will flower in an average of about 60 to 70 days.
Size: Large; about 14 to 18 cm. in diameter.
Borne: 6 to 8 blooms on a single stem and in a compact raceme.
Shape: Flat to slightly cup-shaped with the tepal tips slightly recurved.
Tepalage:
*Number.*—Six.
*Arrangement.*—Overlapping, upper tepals 60° from lower tepals.
*Color.*—The base color is Yellow, RHS 12A, each tepal having a flush of Gold, RHS 21A, about 2 cm. wide and 2 cm. long extending from the upper end of the nectary, along the tepal midrib, for about one-third the length of the tepal. The flowers also have a few tiny pigmented papillae in the extreme center of the flower only and parallel to the light green nectary furrows.
*Spotting.*—A few tiny magenta spots occur in the base portion of the tepals on each side of the nectary.
*Color change.*—The flower color is unusually long lasting and as the flowers age, the color intensifies slightly and may become more golden toned, especially under low light levels.
*Tepal persistence.*—Tepals stay on the stem about three weeks.
Pedicels:
*Character.*—Ascending at about a 45° angle from vertical.
*Length.*—About 6 to 10 cm.
*Form.*—Sturdy.
*Color.*—Light green.
Fragrance: None.
Persistence: The flower is long-lasting, about 2 to 3 weeks both on the plant and as a cut-flower.
Disease resistance: In general, both flower and plant are resistant to disease and in particular, they are resistant to Fusarium and Botrytis, as observed in western Oregon plantings.

THE REPRODUCTIVE ORGANS

Stamens:
*Number.*—Six.
*Arrangement.*—Typical of genus Lilium.
Anthers:
*Color.*—Greyed Gold, RHS 167A.
Filaments:
*Length.*—About 5 cm.
*Color.*—Ivory or yellow.
Pollen:
*Color.*—Same as anthers.
Pistils:
*Number.*—One.
*Length.*—About 5 cm.
Stigma:
*Color.*—Light green to soft plum.
Ovary: Typical of genus Lilium.

THE FRUIT

Fertility: The fruit is fertile.
Shape: Ovoid
Color at maturity: Soft brown sometimes overlaid with light plum.

As does its companion "Vanessa" (Ser. No. 710,496, filed herewith), this new variety of hybrid Asiatic lily most nearly resembles the variety "Connecticut King" (unpatented) but has better bud color and spacing of the inflorescence with tepals that are much broader and of greater thickness and having a few tiny spots in the center of the flower. My new lily variety also does not show the tendency to bud blast upon forcing as does "Connecticut King" and when field cultivated, it attains large bulb size much earlier in the season with earlier flowering than does "Connecticut King", thereby extending the cut-flower season for this type lily.

Distinguishing Characteristics of Siblings From the Cross *Lilium Wilsonii* var. *flavum* × "Connecticut King"

| Cv | Days to Bloom | Buds | Maculation |
|---|---|---|---|
| Pollyanna Serial No. 710,427 | 80–85 | 5–8 | Heavy, large, light. |
| Joanna Serial No. 710,457 | 80 | 5–7 | Light |
| Adelina Serial No. 710,614 | 80–85 | 6–8 | Very few and small. Of deep magenta color. |
| Vanessa Serial No. 710,496 | 90–95 | 5–8 | Very light |
| Yolanda Serial No. 710,577 | 95–100 | 5–8 | Sparse and of deep magenta color. |
| Gold Medal (Half Sib) Serial No. 710,592) | 60–70 | 6–8 | Few tiny |

| Cv | Other Notable Characteristics |
|---|---|
| Pollyanna Serial No. 710,427 | Relatively narrow, widely spaced tepals and sepals with very little marginal overlapping. Arrangement, hexagonal. |
| Joanna Serial No. 710,457 | Tepal-sepal angle 60°. Arrangement, generally imbricated. |
| Adelina Serial No. 710,614 | Tepals are large, thick textured, relatively broad, and with lightly recurved tips. Arrangement, imbricated. |
| Vanessa Serial No. 710,496 | Tepals have slightly recurved tips and inconspicuous maculation. Arrangement, uniformly imbricated. |
| Yolanda Serial No. 710,577 | Larger bulb, flower dished with tepal-sepal angle 60°, with lightly overlapping arrangement. |
| Gold Medal (Half Sib) Serial No. 710,592) | Very thick and broad tepals in 60° overlapping arrangement with sepals, Unusually long lasting flowers, bud blast resistant when forced, and attains large bulb size only in season. |

I claim:

1. A new and distinct variety of hybrid Asiatic lily, substantially as herein shown and described, characterized by its unique yellow and gold flower color pattern and the excellence of its flower form and substance, as well as its versatility both as a garden plant and as a plant produced from precooled bulbs forced for cut flower production.

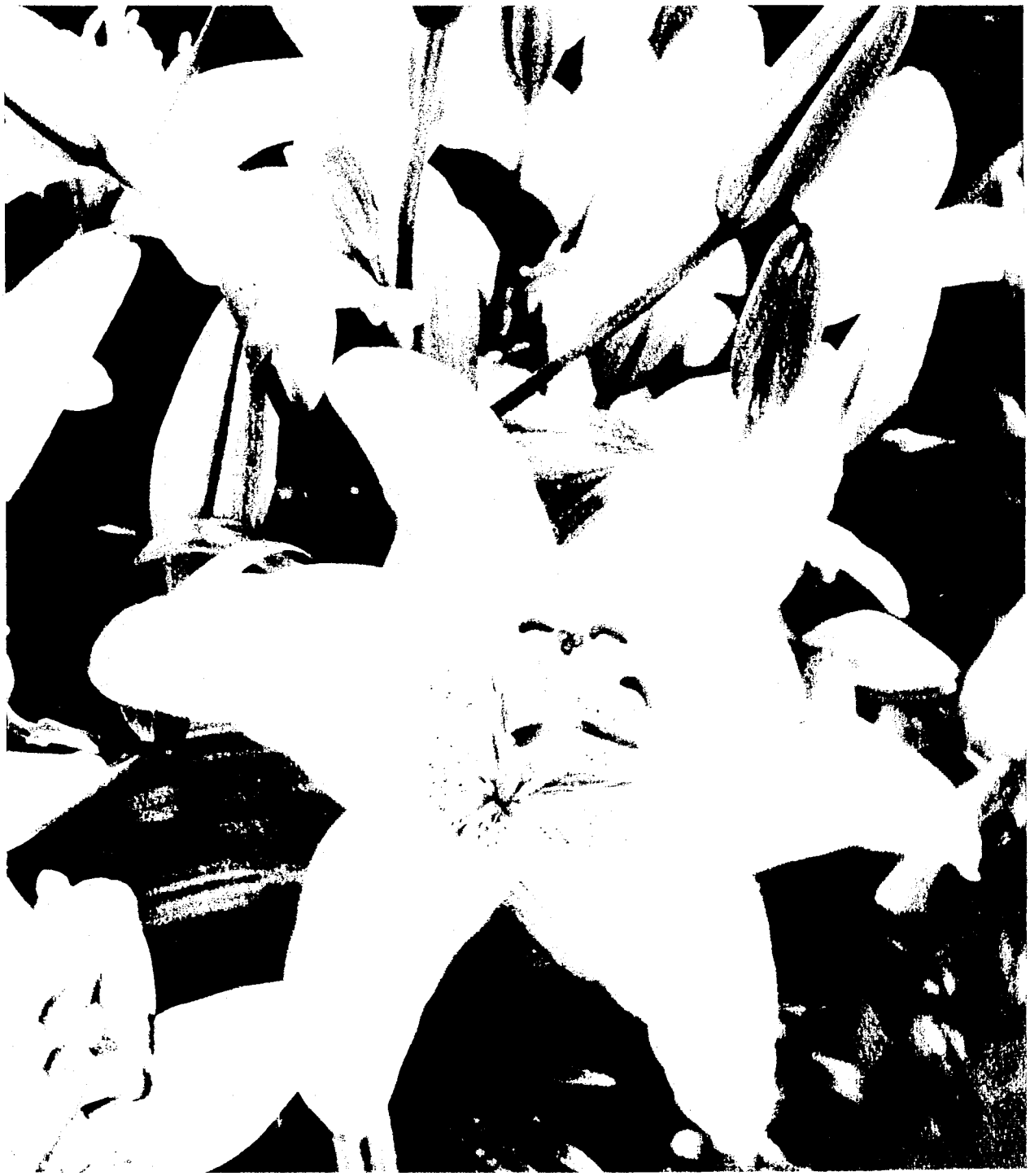

* * * * *